United States Patent
Sanders, III et al.

(10) Patent No.: US 10,863,946 B2
(45) Date of Patent: *Dec. 15, 2020

(54) RESPIRATORY MOTION ESTIMATION IN PROJECTION DOMAIN IN NUCLEAR MEDICAL IMAGING

(71) Applicant: Siemens Medical Solutions USA, Inc., Malvern, PA (US)

(72) Inventors: James Chester Sanders, III, Nuremburg (DE); Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/513,893

(22) Filed: Jul. 17, 2019

(65) Prior Publication Data

US 2019/0336079 A1 Nov. 7, 2019

Related U.S. Application Data

(63) Continuation of application No. 15/721,166, filed on Sep. 29, 2017, now Pat. No. 10,398,382.

(Continued)

(51) Int. Cl.
*A61B 5/00* (2006.01)
*G06T 7/30* (2017.01)
*A61B 6/03* (2006.01)
*A61B 6/00* (2006.01)
*G06T 11/00* (2006.01)

(52) U.S. Cl.
CPC ............ *A61B 5/721* (2013.01); *A61B 5/0035* (2013.01); *A61B 6/037* (2013.01); *A61B 6/5205* (2013.01); *A61B 6/5264* (2013.01); *G06T 7/30* (2017.01); *G06T 11/005* (2013.01); *G06T 2211/412* (2013.01); *G06T 2211/424* (2013.01)

(58) Field of Classification Search
CPC ..... A61B 5/721; A61B 6/5264; A61B 6/5205; A61B 6/037; A61B 5/0035; G06T 11/005; G06T 7/30; G06T 2211/424; G06T 2211/412

See application file for complete search history.

(56) References Cited

U.S. PATENT DOCUMENTS 9,058,692 B1 * 6/2015 Grady .................. G06T 7/0014
2010/0264922 A1 10/2010 Xu (Continued)

OTHER PUBLICATIONS

Chan, Chung, et al. "Event-by-event respiratory motion correction for PET with 3D internal-1D external motion correlation." Medical physics 40.11 (2013).

(Continued)

*Primary Examiner* — Jerome Grant, II

(57) ABSTRACT

In nuclear medical imaging, respiratory motion is corrected. Rather than pairwise estimation of motion from projection views, a sequence-based technique is used to jointly estimate parameters for a motion model across many projection views. In one approach, this sequence-based method is iteratively solved with a maximum likelihood objective function incorporating the motion model. A surrogate respiration signal is used to gate for the joint estimation and used to convert gated motion parameters to temporal motion parameters.

20 Claims, 5 Drawing Sheets

Related U.S. Application Data

(60) Provisional application No. 62/417,023, filed on Nov. 3, 2016.

(56) References Cited

U.S. PATENT DOCUMENTS

| | | | |
|---|---|---|---|
| 2013/0195247 A1* | 8/2013 | Rau | A61N 5/1037 378/65 |
| 2016/0095565 A1* | 4/2016 | Fenchel | A61B 6/527 600/408 |
| 2017/0328970 A1* | 11/2017 | Bi | G01R 33/5676 |
| 2017/0337682 A1* | 11/2017 | Liao | G06T 7/30 |
| 2018/0116596 A1 | 5/2018 | Sanders et al. | |
| 2018/0226596 A1* | 8/2018 | Moriwaki | H01L 51/5234 |
| 2018/0368721 A1 | 12/2018 | Ahn | |
| 2019/0130572 A1* | 5/2019 | Zhang | G06T 7/00 |
| 2019/0332881 A1* | 10/2019 | Hoshino | G06K 9/3241 |
| 2020/0258227 A1* | 8/2020 | Liao | G06T 7/30 |

OTHER PUBLICATIONS

Gratadour, D., L. M. Mugnier, and D. Rouan. "Sub-pixel image registration with a maximum likelihood estimator-Application to the first adaptive optics observations of Arp 220 in the L $/\prime$ band." Astronomy & Astrophysics 443.1 (2005): 357-365.

Guillaume, Mireille, et al. "Maximum-likelihood estimation of an astronomical image from a sequence at low photon levels." JOSA A 15.11 (1998): 2841-2848.

McClelland, Jamie R., et al. "Respiratory motion models: a review." Medical image analysis 17.1 (2013): 19-42.

Sanders, James C., et al. "Fully automated data-driven respiratory signal extraction from SPECT images using Laplacian Eigenmaps." IEEE transactions on medical imaging 35.11 (2016): 2425-2435.

M. Dawood, et al., "Lung Motion Correction on Respiratory Gated 3-D PET/CT Images", IEEE Transactions on Medical Imaging, vol. 25, 2006.

H. Ue, et al., "Nonlinear Motion Correction of Respiratory-Gated Lung SPECT Images", IEEE Transactions on Medical Imaging, vol. 25, 2006, pp. 486-495.

J. Dey, et al, "Non-rigid Full Torso Respiratory Motion Correction of SPECT Studies", in IEEE NSS/MIC, pp. 2356-2358, 2010.

J. Dey, et al, "Estimation and Correction of Cardiac Respiratory Motion in SPECT in the Presence of Limited-Angle Effects due to Irregular Respiration", Medical Physics, vol. 37, 2010, pp. 6453-6465.

* cited by examiner

RESPIRATORY MOTION ESTIMATION IN PROJECTION DOMAIN IN NUCLEAR MEDICAL IMAGING

RELATED APPLICATIONS

The present patent document is a continuation of U.S. patent application Ser. No. 15/721,166, filed Sep. 29, 2017, which claims the benefit of the filing date under 35 U.S.C. § 119(e) of Provisional U.S. Patent Application No. 62/417,023, filed Nov. 3, 2016, which is hereby incorporated by reference.

BACKGROUND

The present embodiments relate to nuclear medical imaging. Example nuclear imaging modalities include single photon emission computed tomography (SPECT) and positron emission tomography (PET). A radioactive substance is administered to a patient. An imaging detector detects the γ-radiation emitted from the patient. The detected emissions are tomographically reconstructed to generate an image object of locations of the emissions in a patient. Due to respiration motion during detection, the reconstructed image object may include motion artifacts or be blurred.

In SPECT imaging, respiratory motion causes blurring and artifacts in reconstructed images due to projection durations that approach or exceed the length of a respiratory cycle. If a respiratory surrogate signal is available that describes the patient's respiratory state over time, gating may subdivide the acquired data into segments within which respiratory motion is small. Reconstructed gates have less respiratory motion artifacts, but the subdivision of counts reduces signal-to-noise ratio (SNR) in these images. For this reason, motion correction allowing use of more data per image is desirable, which, in turn, requires an estimation of the patient's respiratory motion. Correcting for respiratory motion is very difficult due to the high noise and low resolution of SPECT imaging.

Prevailing methods to estimate respiratory motion rely on reconstructing gated images and using 3D-3D registration or optical flow methods to estimate motion fields between these states. These fields may then be either applied directly to the gated reconstructions to deform and sum them or may be incorporated into the projection operator for a new motion corrected reconstruction. The computational runtime necessary to perform a series of independent reconstructions, as well as issues arising from the irregularity of patient breathing, make these methods inconsistent. Data from some gates may be count-deficient or completely missing at certain view angles, resulting in poor quality gated reconstructions that hinder the 3D-3D registration process.

A motion model may be used to reduce the number of estimable parameters needed to calculate motion characteristics and stabilize motion estimates. Due to the difficulty in determining necessary parameters, these models are usually either based on averages over groups of patients or trained using high quality 4-D computed tomography (CT) or magnetic resonance (MR) data acquired prior to the acquisition being motion corrected. The former case does not allow for inter-patient variations in respiratory motion and assumes that the same motion model is valid for all patients. The latter case assumes that a patient-specific model will be constant at two consecutive imaging time points, which may be days apart. Both cases are incapable of adapting to changes in respiration that may occur as the nuclear imaging acquisition progresses.

An alternative for cases where respiratory motion may be described sufficiently in the projection space is to estimate motion using a series of 2D-2D registrations at each projection view. These 2D motion fields may be applied directly to the data prior to reconstruction or passed to the projection operator. In either case, the issue of irregular breathing is mitigated, and computation time may be spared. Nuclear imaging suffers from image noise, and image noise may destabilize the motion estimates.

SUMMARY

By way of introduction, the preferred embodiments described below include methods, systems, and non-transitory computer readable media for correction of respiratory motion in nuclear medical imaging. Rather than pairwise estimation of motion from projection views, a sequence-based technique is used to jointly estimate motion across many projection views. Rather than estimating motion directly, the parameters of a motion model are determined. In one approach, this sequence-based method is iteratively solved with a maximum likelihood objective function incorporating the motion model. A respiratory surrogate signal is used to gate for the joint estimation and used to convert gated motion parameters to temporal motion parameters.

In a first aspect, a method is provided for correction of respiratory motion in a nuclear medical imaging system. A nuclear imaging detector detects emissions over time from a patient. The detected emissions represent projection data and are subject to respiration motion of the patient. The projection data is gated into three or more sets. The respiration motion is estimated with an iterative solution of a maximum likelihood objective function based on the gated projection data of the three or more sets. The objective function includes a motion model of parameters of the respiration motion. The projection data is corrected as a function of the estimated respiration motion. An image object of the patient is reconstructed from the corrected projection data. An image of the reconstructed image object is generated.

In a second aspect, a method is provided for correction of respiratory motion in a single photon emission computed tomography (SPECT) medical imaging system. SPECT emission data of a patient is respiration gated with a surrogate respiration signal into respiration gated sets of SPECT emission data. Two-dimensional motion vectors are jointly estimated across the respiration gated sets of SPECT emission data. Respiration motion is determined as a function of time from the surrogate respiration signal and the two-dimensional motion vectors from each gate. A SPECT image of the patient is generated from the SPECT emission data and the respiration motion.

In a third aspect, a nuclear imaging system is provided. A detector is for detecting signals along lines of response from a patient. A motion processor is configured to determine a respiration surrogate signal form the signals, gate the signals with the respiration surrogate signal into three or more gated sets, and jointly solve for motion in all the gated sets with iterative solution based on a motion model of the motion. A reconstruction processor is configured to reconstruct an image of the signals from the patient, the image being a function of the motion used in reconstruction or used in correction of the signals. A display is configured to display the image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 4A shows motion blurred, noisy data, FIG. 4B shows an image corrected with true shifts, FIG. 4C shows a solution using maximization of pairwise cross-correlations, FIG. 4D shows a solution using minimization of sum of squared differences, and FIG. 4E shows a solution using joint estimation of motion model parameters;

DETAILED DESCRIPTION OF THE DRAWINGS AND PRESENTLY PREFERRED EMBODIMENTS

The flexibility and potential reduction in estimation bias available by pairwise motion tracking is combined with the stability offered by surrogate-signal driven motion models. This is accomplished by fitting the parameters of a motion model using a sequence of respiratory gated projection frames. Instead of a series of pairwise registrations to a reference gate which only consider a portion of the data, a joint estimation takes advantage of all or most available data at each projection step. The estimated model parameters are used, together with a respiratory surrogate signal, to obtain a motion estimate. Two-dimensional (2D) motion in the projection space of SPECT images is used for respiratory motion correction.

A patient-specific motion model whose parameters are estimated at each projection allows for inter- and intra-patient variation in respiratory motion characteristics. The use of a motion model allows for a reduction in estimated parameters, and a joint estimation technique allows all data to be used at once for motion estimation. These two additions to the standard 2D pairwise technique may provide low bias and provide more stable results with lower variance. Applying a motion model to pairwise motion tracking fails to realize the benefits by ignoring large portions of the data during each independent pairwise estimate (e.g. only 20% are considered in the five-gate case). Using the joint estimation scheme in pairwise motion tracking without a motion model, while utilizing all the available data, fails to reduce the number of estimable parameters and thus also does not realize gains in stability.

Figure 1:
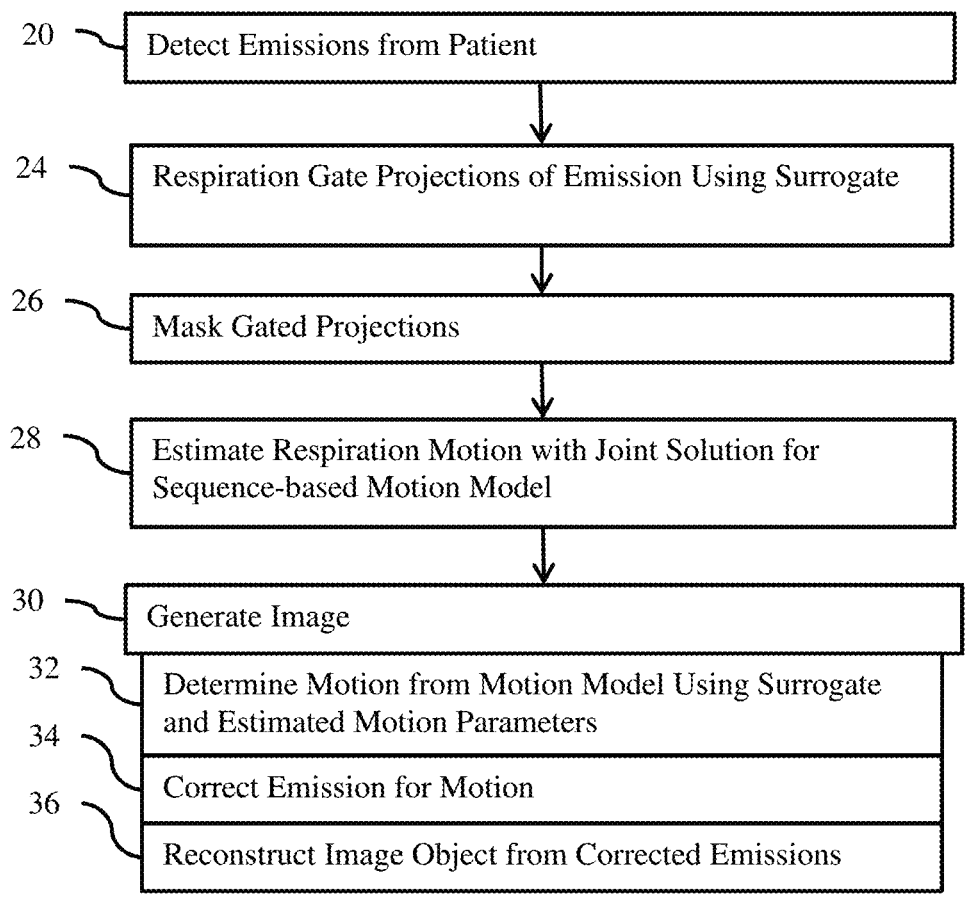
FIG. 1 is a flow chart diagram of one embodiment of a method for correction of respiratory motion in a nuclear medical imaging system.

FIG. 1 shows one embodiment of a method for correction of respiratory motion in a nuclear medical imaging system, such as a SPECT system. Joint estimation of motion in gated projections using a motion model provides motion used to correct the locations assigned to the projections or lines of response of the detected emissions. By correcting the projection data for motion, an image object reconstructed from the motion corrected projection data may have less blur or motion artifact. Alternatively, the motion is used in the projection operator for or during reconstruction.

Figure 8:
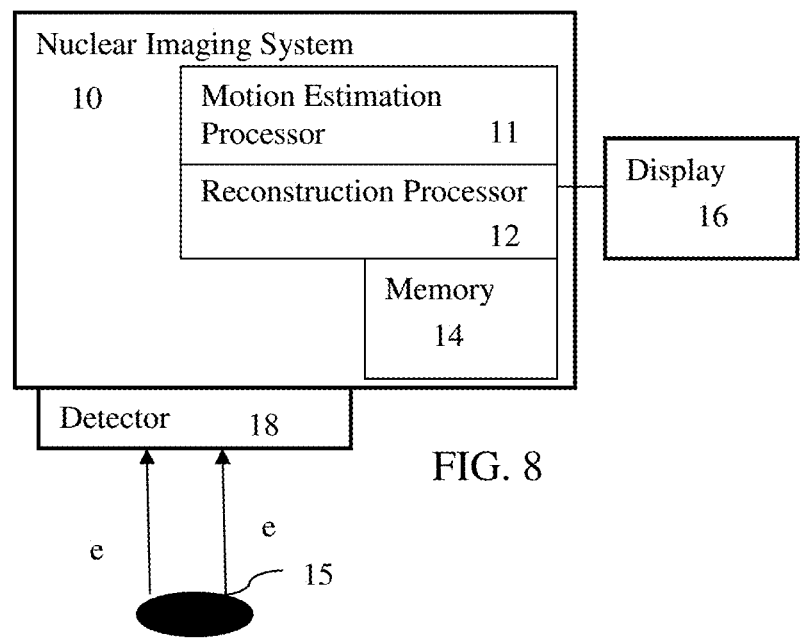
FIG. 8 is a block diagram of a nuclear imaging system, according to one embodiment, for respiration motion correction.

The method is implemented by a nuclear imaging system, such as the nuclear imaging system of FIG. 8. A PET or SPECT imaging system may be used. In the examples below, SPECT is used. A detector, such as a gamma camera or ring of detectors, detects emissions in act 20, one or more image processors performs acts 24-30, and a display, memory interface, or network interface may be used for act 30. Other devices may be used to perform any of the acts, such as a graphics processing unit and/or reconstruction processor.

The acts are performed in the order shown (e.g., top to bottom or numerical) or other orders. For example, the correction of act 34 may be part of the reconstruction of act 36 where the estimated motion is used in the system matrix or projection operator for reconstruction.

Additional, different, or fewer acts may be performed. For example, act 20 is not provided where the detected emissions are stored or transferred from memory. As another example, act 26 may not be provided. In other examples, act 30 is not provided, and the motion estimate is used for other purposes than imaging. Acts for configuring the imaging system or use of results may be provided.

In act 20, emissions from a patient are detected. After ingesting or injecting a radiotracer into the patient, the patient is positioned relative to a detector, and/or the detector is positioned relative to the patient. Emissions from the radiotracer within the patient are detected over time. A collimator in front of the detector limits the direction of photons detected by the detector, so each detected emission is associated with an energy and line of response (e.g., a cone of possible locations from which the emission occurred). The detection along lines of response forms projection data, data representing emissions along lines generally perpendicular to the detector. The depth of the emission from the detector is not known.

For SPECT, the detector may be rotated or moved relative to the patient, allowing detection of emissions from different angles and/or locations in the patient. For multi-camera SPECT, emissions may be detected at a same time using cameras at different angles relative to the patient. In PET embodiments, the detector is formed in a ring so that coincidence is used to detect the same emission from different directions along the lines of response.

The detector includes direct detection with CZT or indirect conversion (e.g., NaI, LSO layered scintillation crystal) using photomultiplier tubes, SiPM, or other photon detectors. For SPECT, detectors are arranged along a rectangular or other grid to provide a two-dimensional planar array for detecting gamma radiation along lines of response corresponding to the cells or pixels of the planar array. For PET, the photomultiplier tubes are arranged in a ring around a patient. Other types of detectors may be used, such as any gamma detector.

The emissions over time are detected. Due to the detection along lines of response, the detections constitute projections of the emissions. By detecting at different locations (e.g., pixels in a SPECT detector), projection data (e.g., no depth or limited depth information) distributed over multiple dimensions is provided. For example, a SPECT detector at one location relative to the patient generates projection data distributed along two dimensions of the planar SPECT detector.

Since the detection of emissions takes many seconds or minutes to gather sufficient data to avoid or limit artifacts due to poor SNR, the detected emissions are subject to respiration motion of the patient. As the patient is scanned, the patient breathes. This respiration motion causes parts of the patient to shift so that a detection from one location in the patient is at one pixel of the detector at one time, but another pixel of the detector at another time. The resulting projection data even with a same position of the detector relative to the patient is subject to blurring due to respiration motion.

In act 24, the projection data is respiration gated. Although a motion estimation at the time resolution of the imaging system is possible, the low clinical count rates may result in poor SNR. Respiratory gating may improve SNR.

Any number of gates may be used. For example, three or more (e.g., five or eight) sets of respiration gates are used. Each gate represents a part of the respiration cycle, so that projection data subjected to similar motion or location shift is grouped together.

In gating, the respiration cycle is divided into non-overlapping surrogate signal amplitude or cycle phase ranges. Each detected emission is assigned to one of the gated sets of data. For each gate, a set of data is formed. The gated sets of projection data from the detected emissions form respiration gated sets of SPECT emission data.

The gating is performed with a surrogate respiration signal. Any source or measure of the respiration cycle of the patient may be used, such as a breathing sensor, pressure sensor, or motion sensor. In one approach, the surrogate respiration signal is derived from variation in the projection data as a function of time. Before gating, the projection data over time is analyzed to determine variation as a function of time. In one embodiment, the projection data is in a listmode data format. At each SPECT camera stop, data is initially binned into 200 ms frames, yielding a sequence $g_t(y)$, where t is time and y the projection data. The respiratory surrogate signal is estimated by reducing the dimensionality of the data frames, resulting in a one-dimensional temporal sequence of amplitude variation. This variation is the surrogate signal then used to drive amplitude-based gating to re-aggregate the bins or projection data into the respiratory gates (e.g., K=5), thus yielding the sequence $g_k(y)$, where k is the gate number. Other gating may be used.

Amplitude-based gating may temporally subdivide the input projection data into gates such that each gate has an equal or similar number of counts. This equal or similar distribution allows an increased SNR in each gated set, $g_k(y)$, of projection data, while still fulfilling the condition that motion within the gate is small. Other amplitude or phase variation approaches may be used.

For each gate, a frame or set of projection data is provided. For SPECT, the set of projection data represents a two-dimensional spatial array of counts or emissions for one camera position of the SPECT detector. The detected emissions for the range of times or cycle phase of the gate are collected and form the gated projection image.

Separate gating is performed for different SPECT detector positions or angles relative to the patient. The projection data from each SPECT detector or camera is handled separately. In one embodiment using a dual detector system, projection data from each camera position for two simultaneously-acquired projections with a dual SPECT camera system are considered independently. Prior to motion estimation, the raw data are subdivided into K respiratory gates and scatter-corrected. Alternatively, the data from cameras 180 degrees apart may be combined. The iterative solution is performed independently for each camera position. In the case where the angular separation between detectors is 180°, data from one detector is reflected across the vertical axis and added to data from the other detector. The two detectors observe the same motion. For cases such as cardiac imaging, where the angular separation may be less than 180°, estimation of the horizontal motion parameters for both detectors is carried out separately.

In act 26, the image processor or other processor masks the projection data. Each gate or set of projection data is masked. Different masks are provided for the different gates or a same mask is used for two or more (e.g., all) of the gates. The mask is based on projection data for one gate or for multiple gates. In alternative embodiments, masking is applied prior to gating (e.g., on a collection of all the detected emissions) or masking is not used.

The masking removes data that is likely noise or not of interest. Background activity that might hinder recovery of the motion of the object(s) of interest is reduced or removed. The count for the location to be removed is reduced or set to zero.

Image processing determines the locations of the background activity. For example, a thresholding with or without spatial low pass filtering is applied to create a binary mask. In one embodiment, the masking is a function of a shape, such as an ellipsoid, fit to the projection data of the gate. For example, in hepatic (e.g., liver) imaging, sums over the horizontal and vertical dimensions are calculated. The full width at 10% of the maximum (FWTM) of the resulting marginalizations is computed. An ellipsoid is defined in the projections of the gates centered at the center of mass (CoM) with the horizontal and vertical widths corresponding to the measured FWTM along these axes. Other masking approaches may be used, such as detecting gradients to identify boundaries or iso-contours separating background from counts of interest.

The projection data may be processed in other ways before or after gating and/or masking. For example, spatial or temporal filtering is applied. As another example, scatter correction is applied.

In act 28, the image processor or other processor estimates the respiration motion. The goal is to estimate rigid translations $\beta_k = [\beta_{1,k} \ \beta_{2,k}]^T$ along the horizontal and vertical axes of the projection space at gate k. Non-rigid translation may be used in other embodiments, such as by separately determining rigid translations for patches of the projection data for the gate. The rigid translations for each of the gates is to be determined as the different gates represent the counts from different phases of the respiratory cycle.

In one embodiment when a linear motion model is being used, the shifts become $\beta_k = \bar{s}_k(t) \cdot \theta$ where $\bar{s}_k(t)$ is the mean value of a surrogate respiratory signal at all time points allocated to the $k^{th}$ gate and the vector $\theta$ contains the parameters of motion (e.g., scaling factors that, when multiplied by the surrogate signal yield shifts along two perpendicular dimensions). It is possible for the shifts $\beta_k$ to be embedded as elements of a matrix $M_k$ defining the motion at a given gate k. Once the parameter set, $\theta$, of the motion has been estimated, $M_t$ is obtained at arbitrarily fine time resolution to be applied for motion correction. Thus, the respiration motion as a function of time is obtained from the estimated parameters set, $\theta$, defining the motion based on the motion for the gate.

Rather than pairwise estimation of motion, the estimation is joint. The two-dimensional motion vectors are jointly estimated across the respiration gated sets of SPECT emission data. The rigid motion is parameterized as horizontal and vertical or along other perpendicular axes. Other motion parameters than two-dimensional motion vectors may be estimated, such as scale and/or rotation.

The joint estimation uses an iterative solution with an objective function. The objective function includes a motion model formed by the parameters representing the respiration motion. Various motion models may be used. For example, a linear model with two parameters (e.g., horizontal and vertical motion) is used. A reduced order model may be used, such as reducing the two parameters to a single parameter. A higher order model may be used, such as including rotation and/or scale parameters.

As respiratory gating is accomplished by a respiratory surrogate signal s(t), this surrogate signal may be used as the input to the motion model to reduce the number of parameters to be estimated. A further advantage of a motion model is that the model enables motion correction to be carried out at the temporal resolution of the surrogate signal, which may be much higher than that of the respiratory gates. This motion may be represented as:

$$M_t = \phi(s(t), \theta), \quad (1)$$

where $M_t$ is a motion field, and $\phi$ is the motion model, which is a function of the surrogate signal over time and the parameters in $\theta$. Given the model and associated parameters, data acquired at each time point t may be shifted back to a reference point using $M_t$.

Given the gated projections, the motion model is represented in gate space rather than time. A matrix $M_k \in \mathbb{R}^{3 \times 3}$ represents the transformation of a point in the $k^{th}$ gated projection $g_k(y)$ to one in a reference projection $g_{ref}(y)$ such that $g_{ref}(y) = g_k(y')$ using homogeneous coordinates as follows:

$$M_k y = y' = \begin{bmatrix} 1 & 0 & \beta_{1,k} \\ 0 & 1 & \beta_{2,k} \\ 0 & 0 & 1 \end{bmatrix} \begin{bmatrix} y_1 \\ y_2 \\ 1 \end{bmatrix} = \begin{bmatrix} y_1' \\ y_2' \\ 1 \end{bmatrix} \quad (2)$$

where $g_k(y')$ is the motion corrected data from gate k. The translation is linearly related to the respiratory surrogate signal. A linear motion model is followed to calculate the shift parameters at each time point, represented as follows:

$$M_t(\theta) = \begin{bmatrix} 1 & 0 & \theta_1 s(t) \\ 0 & 1 & \theta_2 s(t) \\ 0 & 0 & 1 \end{bmatrix} \quad (3)$$

The motion model consists of vertical and horizontal shifts that are assumed to be linearly related to the surrogate signal. $\theta$ is to be fit on a patient-by-patient basis to allow for data-driven surrogate signals. The horizontal x and vertical y shifts of the model may be calculated simply as $m_x(t) = \theta_1 \cdot s(t)$ and $m_y(t) = \theta_2 \cdot s(t)$, respectively. This framework also leaves open the possibility of estimating a separate parameter set $\theta_p$ independently for each camera stop p, which allows the method to better adapt to variations in patient breathing motion throughout the acquisition.

For a joint solution, the rigid motion between three or more gated sets is solved for simultaneously. The joint solution determines the values for the motion model parameters across three or more (e.g., all) of the gated projections. Using this sequence-based approach, simultaneous solution for motion across more than pairs of gates of projection data is performed. Due to the high noise present in photon-limited SPECT imaging and even higher noise in individual respiratory gates, estimating motion between pairs of gates may be unstable. Using joint estimation improves stability by using all available data.

The sequence-based method estimates the pair of parameters at each SPECT camera stop. For a dual-head SPECT system, the joint solution may include solving with two simultaneously-acquired projections. Parameters of the motion model are separately determined at each projection view to maximize the ability to adapt to motion variations. Data from all or many projections are used in the solution or objective function, providing higher estimation quality than pairwise estimation or population-based estimation and without the issue of reconstruction artifacts and extra computational load of a series of gated reconstructions. Accuracy of registration for noisy astronomical image sequences may be increased to the sub-pixel regime by performing joint estimation of shifts for the entire sequence simultaneously.

To estimate the model parameters, the influence of noise in the projection may be modeled. Although SPECT data as acquired is Poisson-distributed, the detected emissions may be scatter corrected to enhance contrast prior to motion estimation. Any scatter correction may be used, such as subtraction of spatially smoothed data. This, along with the sub-pixel interpolation in the frequency domain, perturbs this distribution. For this reason, a Gaussian maximum likelihood (ML) formulation is used for the objective function. In alternative embodiments, the Poisson or other distribution is used. In other embodiments, prior knowledge is used for a Bayesian maximization of the posterior probability of the motion parameters instead of a maximum likelihood.

Given a non-blurred, noiseless reference image r(y) and a set of motion model parameters $\theta$, the likelihood of observing a sequence of gated projections $\{g_k(y)\}$ is given as:

$$\mathcal{L}(\{g_k(y)\} \mid r(y), \theta) \propto \Pi_k \Pi_y \exp\left(-\frac{(g_k(y) - r(M_k(\theta)^{-1} y))^2}{2\sigma_k^2(y)}\right) \quad (4)$$

where $\sigma_k^2(y)$ is a map of the data's noise variance, which is approximated as $\sigma_k^2(yy) = \max(g_k(y), 1)$. Other noise variance functions may be used.

In equation 4, the parameter vector $\theta$ is embedded within $M_k(\theta)$, and the reference image is not the same as the reference projection used in pairwise estimation. Instead, the reference projection represents the scene being imaged as the scene would be observed under ideal conditions. In practice, r(y) is unknown. A maximum likelihood estimate of the reference projection given a current estimate of the motion parameters $\hat{\theta}$, and therefore a corresponding sequence of $M_k(\hat{\theta})$, is the mean of gated projections shifted to the reference location, given by:

$$\hat{r}(y, \hat{\theta}) = \frac{1}{K} \sum_k g_k(M_k(\hat{\theta})y) \quad (5)$$

The mean of the gated projection data of the sets in the sequence shifted to a same location is used for the reference. Other reference projections may be used.

The maximum likelihood objective function allows for an iterative solution. By minimizing the maximum likelihood of the gated projection data for the sequence relative to the reference projection, the parameters of the motion model may be estimated. In the iterative solution, the reference projection is updated. In each iteration, the reference projection is updated.

By incorporating equation 5 into equation 4 and taking the negative of the natural logarithm, a negative log likelihood function results, as represented by:

$$l(\{g_k(y)\} \mid \hat{r}(y, \theta'), \theta) = \Sigma_k \Sigma_y \left( \frac{(g_k(y) - \hat{r}(M_k(\theta)^{-1} y))^2}{2\sigma_k^2(y)} \right) \quad (6)$$

where the parameters to be fit $\theta$ are embedded in each $M_k(\theta)$. Fitting to the gated projection data is accomplished by minimizing the objective function over $\theta$. The objective function with the motion model for joint solution over three or more sets of gated projection data (i.e., over the sequence rather than pairwise) is represented as:

$$\theta^* = \mathrm{argmin}_\theta l(\{g_k(y)\} \mid \hat{r}(y,\hat{\theta}),\theta) \quad (7)$$

Other objective functions may be provided.

This objective function is iteratively solved. $r(y, \hat{\theta})$ is updated after each iteration with the current estimate of $\hat{\theta}$. The maximum likelihood objective function of equation 7 is iteratively solved for the joint estimation. The joint solution using the sequence-based method (e.g., three or more gated sets of projection data) finds the parameters (e.g., two-dimensional motion vectors) for motion in the motion model over the cycle. The motion model is simultaneously fit to the projection data across all or most of the respiration gated sets for the given camera position.

Any iterative solution may be used, such as a gradient-based iterative solution. In one embodiment, a Broyden-Fletcher-Goldfarb-Shanno algorithm is used to optimize equation 7.

For the iterative solution, the initial values of the parameters are set. Default values, such as based on a population study, may be used. In one embodiment, the initial value of one or more of the parameters is estimated as a ratio of a largest difference in center of mass between the sets of the gated projection data to a change in amplitude of a surrogate respiration signal over time. Initialization is carried out by first computing the sequence of centers of mass (CoMs) at each gate $\{c_k\}$. The initial estimate of the parameters $\theta^0$ is then set according to:

$$\theta_i^0 = \alpha \frac{\max(\{c_{i,k}\}) - \min(\{c_{i,k}\})}{\max(\{\bar{s}_k(t)\}) - \min(\{\bar{s}_k(t)\})} \quad (8)$$

where i refers to the dimension being initialized and $\alpha \in \{-1,1\}$ is a polarity correction factor set to the sign of the linear correlation between $\{c_{i,k}\}$ and $\{\bar{s}_k(t)\}$. Following initialization, at the $q^{th}$ iteration, the reference image is updated with parameters estimated from the previous iteration: $\hat{r}^q(y,\theta^{q-1})$. Other initializations may be used.

Figure 2:
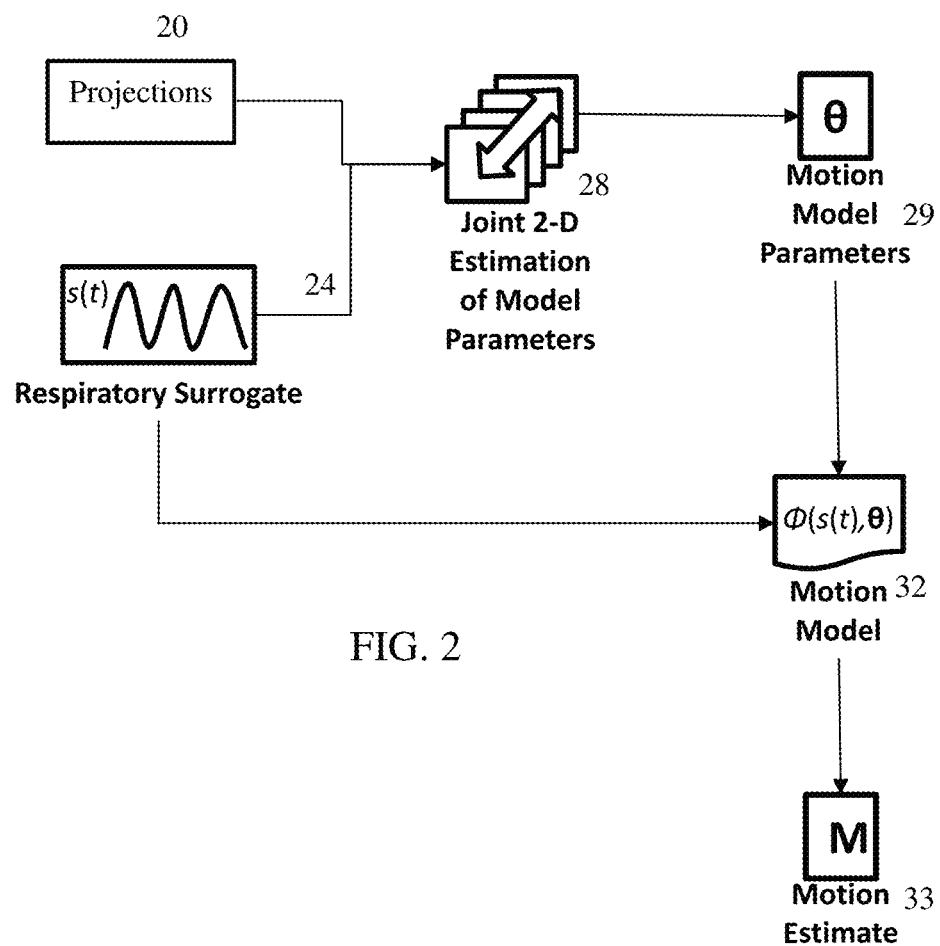
FIG. 2 is a flow chart diagram of another embodiment of the method for correction of respiratory motion in a nuclear medical imaging system.

Once solved, the values for the parameters of the motion model over gates is provided. For example, these values, when multiplied by the surrogate signal s(t), represent the two-dimensional motion vectors for horizontal and vertical motion through the gated sets of projection data. This gate-based motion may be used to determine time-based motion. FIG. 2 shows an example. The projections 20 are used with the surrogate respiratory signal 24 to form gated sets of projection data. The joint estimation of act 28 is performed, solving for the motion model parameters 29. The motion model 32 is completed by combining the surrogate signal 24 with the motion model parameters 29. The motion model may then be used to obtain the motion 33. After scatter correction and estimation of $\theta^*$ using equation 7, the shifts at each time point t are obtained directly using the motion model: $\beta_t(t) = \theta_t^* \cdot s(t)$. The motion model provides the shift for each time rather than each gate (i.e., range of times). Alternatively, the same shift is applied to the detected emissions for each gate. Different shifts are provided for different gates.

Referring again to FIG. 1, the estimated motion is used to generate an image in act 30. Acts 32-36 show one example approach. In this example approach, the motion is used to correct the projection data prior to reconstruction. In an alternative or additional approach, the motion is used with the system matrix or projection operator to account for the motion for or during reconstruction. The motion is used in the reconstruction, applying the motion in image space rather than data space. The reconstruction accounts for the motion while preserving the raw projection data and noise structure.

The image is of the patient. The projection data from the patient is used to generate the image, such as generating the image from SPECT emission data. The respiration motion is also used. The image is a SPECT image showing distribution of activity in the patient. A PET image may be generated. The image is of a two-dimensional or planar slice in the patient. Alternatively, the image is a rendering from volume data to the two-dimensional display, such as using ray casting, path tracing, surface rendering or other three-dimensional rendering.

In the example of acts 32-36, the SPECT emission data is corrected with an inverse of the determined respiration motion as a function of time. In act 32, the respiration motion as a function of time is determined. Where the solution provides motion as a function of cycle phase or gates, the motion is converted to be a function of time. Due to sampling, the gated motion may be low resolution. By combining with the surrogate respiration signal in the time domain with the two-dimensional motion vectors or other motion parameters of the gates, the motion for each detection time is provided. Alternatively, a function, such as a sinusoidal curve, may be fit to the motion for the gates to provide motion as a function of time through the cycle.

In act 34, the projection data is corrected. The estimated respiration motion as a function of time is used to correct. The motion at each time represents a spatial offset. Each emission is detected as being for a line of response at a particular time. An inverse of the motion at that time is applied to the emission, shifting the location or line of response at which the emission is detected. This correction process is applied to each detected emission.

The spatial shift applied to each emission has pixel or sampling grid resolution. The respiratory motion may have sub-pixel or partial pixel or grid shift. Interpolation is used to determine sub-pixel shift. Since a discrete matrix of data is used but sub-pixel shifts are to be estimated, some form of interpolation is used to compute translated projection images for a continuous range of shifts β. In one embodiment, the interpolation is in the Fourier domain. A Fourier transform pair is represented as $g(y-\beta) \Leftrightarrow G(\omega)e^{-j\omega \cdot \beta}$, where $G(\omega)$ is the Fourier transform of $g(y)$ and $j$ is the imaginary number. The projection to be shifted is Fast Fourier Transformed and multiplied by the corresponding complex exponential. Prior to multiplication with the complex exponential, the projection data may be lowpass filtered with a sin c filter. The cutoff spatial frequency is set at 0.0505 cycles/mm, as the SPECT collimator's modulation transfer function suppresses most image content above this frequency. Other cutoff frequencies or filtering may be used.

In act 36, an image object is reconstructed from the corrected projection data. The projection data for each camera position is corrected and then used together for reconstruction. A reconstruction processor reconstructs an image object from acquired, motion corrected projection data from different camera angles. Computed tomography implements reconstruction to determine a spatial distribution of emissions from the detected lines of response. The position of each emission relative to the lines of response is corrected to account for respiratory motion. The corrected projection data represents the detected emissions and the lines of response for those emissions. The quantity or amount of uptake for each location (e.g., voxel) may be estimated as part of the reconstruction. The nuclear imaging system may estimate the activity concentration of an injected radiopharmaceutical or tracer for the different locations.

Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, non-negative least squares (NNLS), or another approach. Different types of reconstruction have different strengths and weaknesses.

The reconstruction provides a three-dimensional representation of the image object. The 3D spatial distribution of emissions is determined. To generate the image, the reconstructed emissions along a plane, slab, or volume are used. The image of the reconstructed image object is generated. The image of the patient or part of the patient is generated from the reconstruction. For qualitative SPECT, this distribution is used to generate an image. For quantitative SPECT, the activity concentration for each location (e.g., voxel) is determined. The reconstruction provides voxel values representing activity concentration. In one embodiment, data for one or more (e.g., multi-planar reconstruction) planes is extracted (e.g., selected and/or interpolated) from a volume or voxels and used to generate a two-dimensional image or images.

The output may be a transmission. The transmission is of the image to a display. The transmission may be to a memory through a memory interface and/or to a patient medical record, server, or other computer connected through a network interface.

Figure 3:
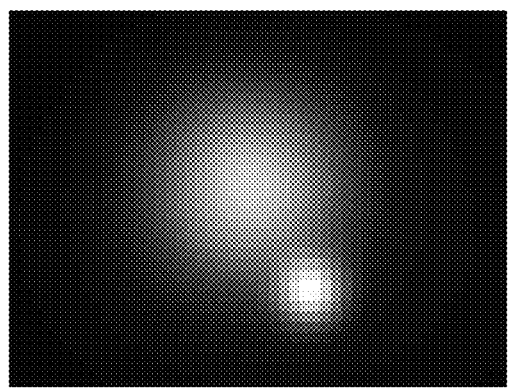
FIG. 3 illustrates a simulation of Gaussian blobs for comparing motion correction techniques.

In a simulation, a projection image composed of three Gaussian "blobs" simulates projection data. The standard deviations and mixing proportions of the Gaussians are set to roughly mimic a Tc99m-MAA liver shunt diagnostic scan with one focal lesion, a region with diffuse elevated activity in the liver, and a background surrounding this area. The source is then blurred with a Gaussian with FWHM of roughly 3 pixels to simulate the point spread function of the imaging system. This truth image is shown in FIG. 3. The image is then translated over time by a squared sinusoidal waveform with peak-to-peak amplitude of 2 pixels in the X direction and 8 pixels in the Y direction to simulate respiration. Poisson noise is added to the resulting image sequence to simulate a respiratory gated clinical acquisition with 10 gates.

Three methods are used to estimate the motion: pairwise maximization of the cross-correlation (CC), pairwise minimization of the sum of squared differences (SSD), and the proposed method using joint maximum likelihood for the sequence-based method and motion model (S-MM). In the CC and SSD implementations, gate one is chosen as reference, and each subsequent remaining gate is sequentially registered to the reference using an exhaustive grid search over all possible motion shifts. For the S-MM approach, equation 7 is minimized numerically using Matlab's fminunc function with an initialization based on motion shifts derived from a centroid measurement in each frame. A normalized version of the true motion waveform is used as a surrogate. This process is repeated for 20 noise realizations to assess the variation in the estimated parameters. A 30 counts/pixel maximum is used.

Figure 4A:
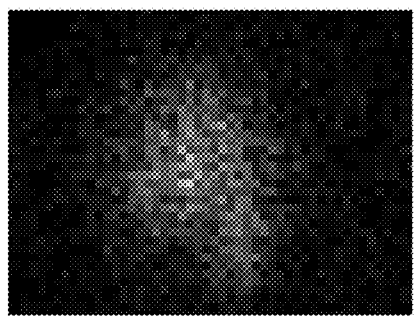
FIGS. 4A-E show example simulation results based on FIG. 3 where
Figure 4B:
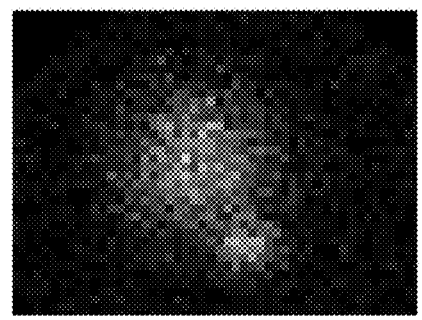
Figures 4C, 4D, 4E:
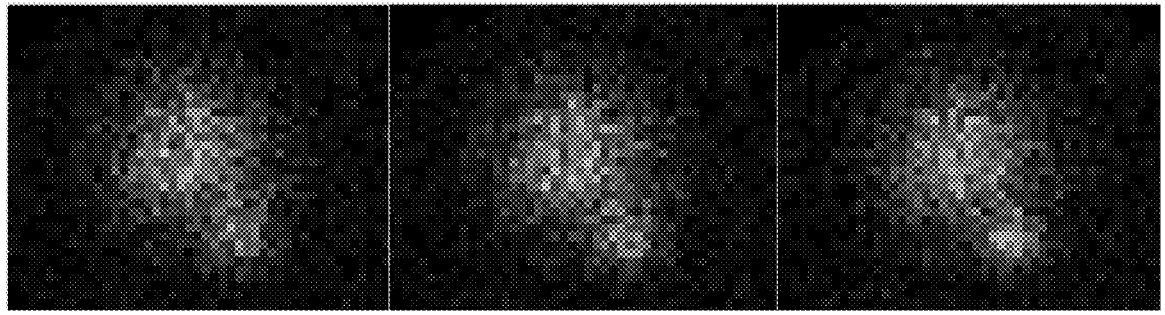

Qualitative results from one noise realization are shown in FIGS. 4A-E. In the motion blurred composite image of FIG. 4A, the differentiation between diffuse and focal blobs cannot be resolved. In the composite image after motion correction with the true shifts of FIG. 4B, the distinction is recovered, and both objects have higher intensities due to the reduction in blur. The CC and SSD solutions of FIGS. 4C and 4D, respectively, are somewhat better than the blurred image of FIG. 4A. The results of motion correction using the S-MM solution is shown in FIG. 4E. The difference between the two blobs is most easily resolved in FIG. 4E as compared to FIGS. 4C and 4D. FIG. 4E is most similar to the true shift image of FIG. 4B. In FIG. 4E, the contrast in the focal area appears higher.

Figure 5:
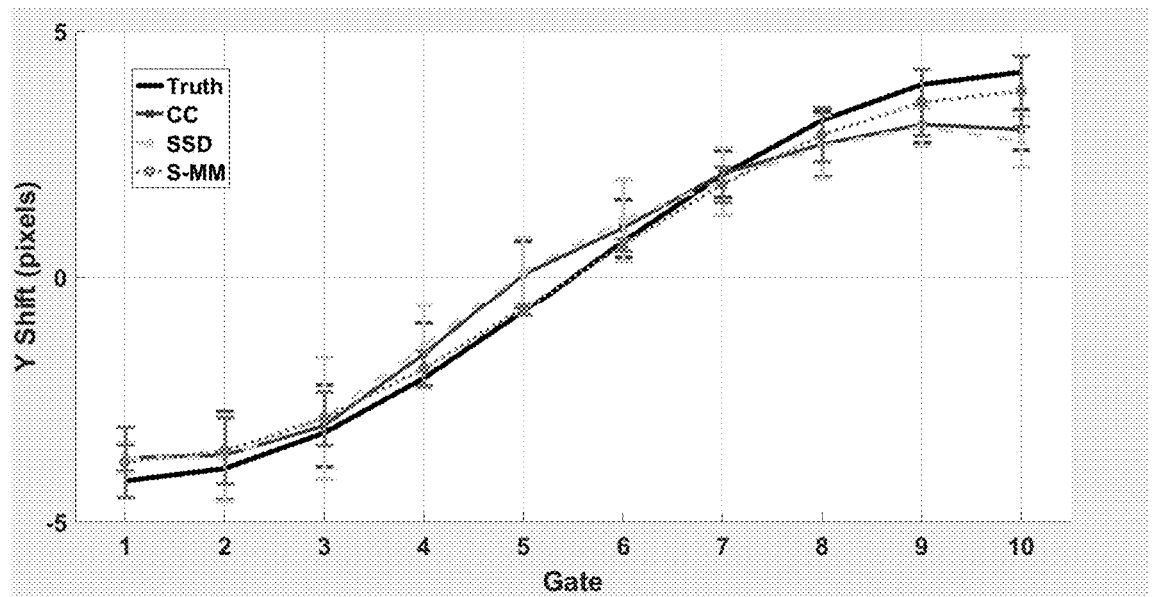
FIG. 5 shows true and mean estimated Y shifts from a simulation study using cross-correlation (CC) and sum of squared differences (SSD) in a pairwise implementation and maximum likelihood in a joint estimation with a motion model (S-MM)

A quantitative summary over the 20 noise realizations is shown in FIG. 5. Here, the true Y shifts are plotted on the solid black curve, and the mean estimated Y shifts for the three methods are shown in the others. The error bars represent ±1 standard deviation over the 20 realizations. Each of the methods underestimates the motion slightly at the positive and negative extremes, but the structure is, in general similar to the true values. The underestimation at the upper extreme is less for S-MM. The variance of the motion estimate for the S-MM (shown as ML) method is less that for the CC and SSD methods, particularly in gates 4-8, where the variance drops to nearly zero for S-MM.

In a patient example, one shunt diagnostic acquisition from a patient is processed using the same S-MM technique as the simulation. The patient is injected intraarterially with 135 MBq Tc-99m-MAA and subjected to a SPECT/CT acquisition on a Symbia T2 (dual camera) with 60 camera stops (120 projections) with a dwell time of 15 seconds. As the two detectors observe the same motion simultaneously and the acquisition is carried out in the 180-degree configuration, projection data from detector two is reflected across the vertical axis and added to that from detector one to yield the data on which the estimation is performed. A data-driven respiratory surrogate is used to gate the data and derive the motion model. Estimated Y shifts at each view are applied to the listmode data using nearest-neighbor interpolation, preserving the Poisson distribution in the data prior to reconstruction. The corrected and uncorrected datasets are attenuation corrected using the system's hardware registration matrix.

Figure 6A:
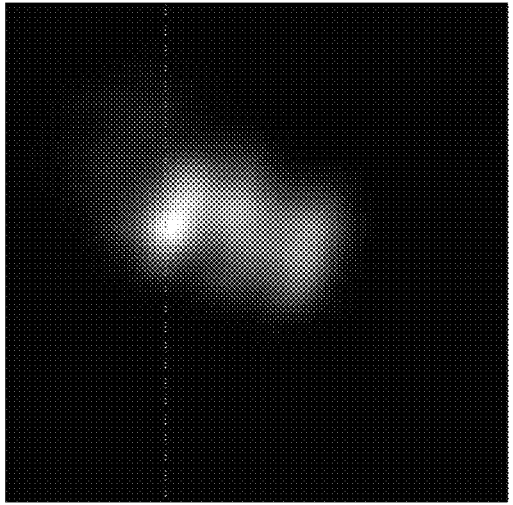
FIGS. 6A and C show uncorrected reconstruction images of one patient from the coronal and sagittal views.
Figure 6B:
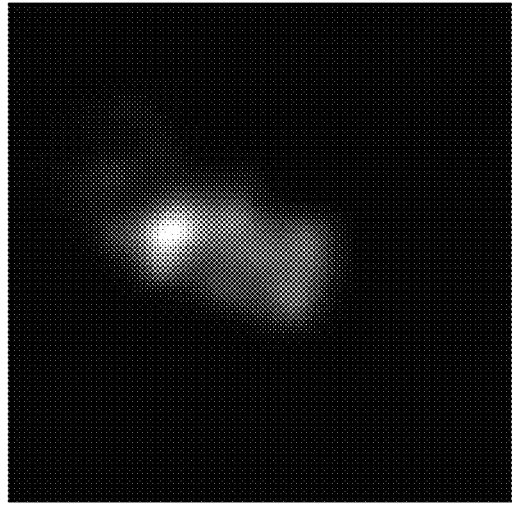
FIGS. 6B and 6D show reconstruction images of the same patient corrected for motion with joint motion estimation.
Figure 6C:
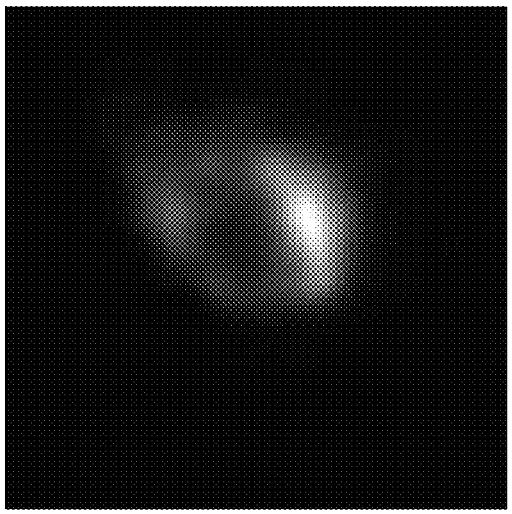
Figure 6D:
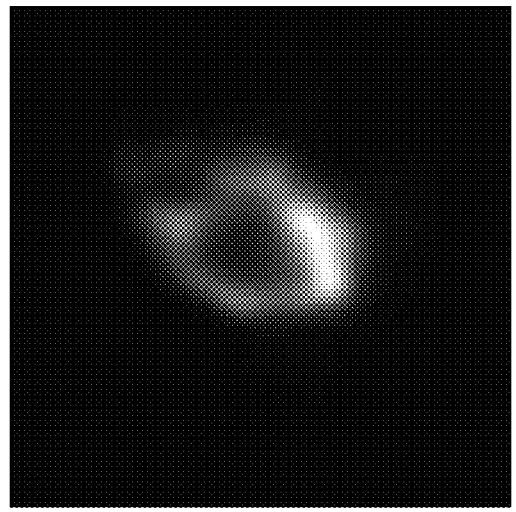
Figure 7:
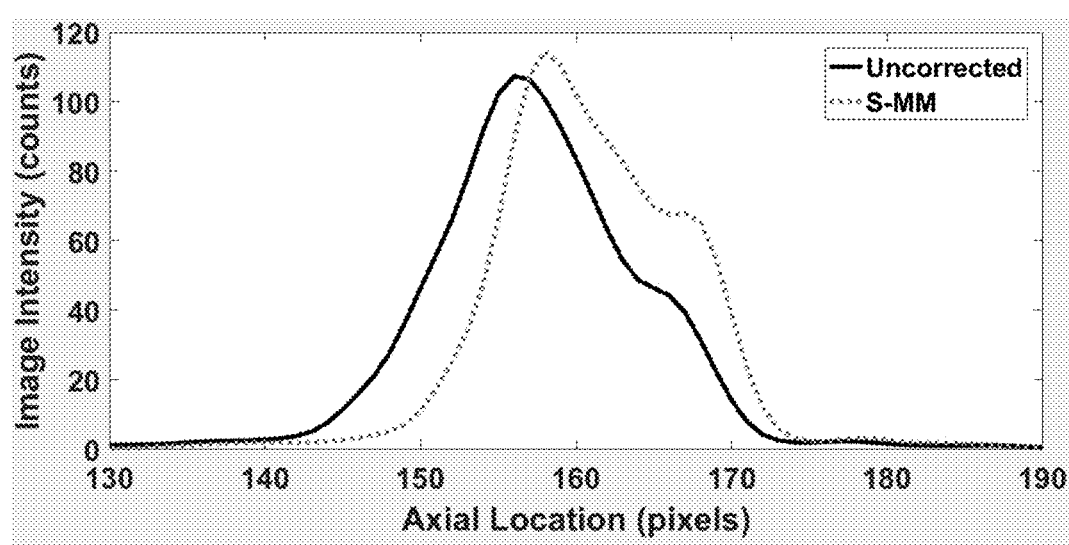
FIG. 7 shows axial profiles from the uncorrected and motion corrected (S-MM) reconstructions drawn along the vertical line shown in FIG. 6A.

Coronal (top row) and sagittal (bottom row) slices from uncorrected (left column) and motion corrected (right column) reconstructions are shown in FIGS. 6A-D. Blurring along the vertical (head/foot) axis in the corrected images of FIGS. 6B and 6D is reduced relative to the uncorrected data of FIGS. 6A and 6C. The fine vascular structures to the left of the lesion in the coronal images are also more clearly visible in the corrected image of FIG. 6D relative to the uncorrected image of FIG. 6C. The line profiles along the vertical lines of FIG. 6 are shown in FIG. 7. The line profiles indicate a higher lesion contrast for motion corrected data and sharper edges at the superior and inferior borders of the liver activity.

The simulation results show that the joint estimation approach in tandem with a motion model reduces variance in the motion estimate while matching the bias of pairwise estimation. Although this simulation is limited, it shows that the method is feasible in a low count/high noise environment capable of delivering stable results. The patient case, while confined to a single example, nevertheless shows the feasibility of the method on real data. Expected reduction of blurring is achieved, and subjective image quality is improved. Due to observed motion shifts, the uncorrected and motion corrected reconstructions may be registered to the CT separately to avoid attenuation correction artifacts arising from emission/transmission mismatches.

In other embodiments, the imaged scene includes other sources of motion, such as from cardiac activity. To limit influence from undesired motion, the object of interest is masked.

In other embodiments, PET data reformatted into the sinogram space may be gated using a respiratory surrogate signal. Joint estimation of motion model parameters may then be carried out using all of the gated sinogram frames. A separate set of parameters may be estimated for each PET bed position. With parameters, the sonogram data may then be motion corrected using the motion model, estimated parameters, and the surrogate signal before reconstruction.

The method estimates the respiratory motion in the projection space of SPECT or PET images. The use of a surrogate signal driven motion model and maximum likelihood-based joint estimation of the model parameters decrease the variance of the motion estimate by reducing the number of parameters that must be estimated and utilizing all or most of the data available at each projection view, respectively.

FIG. 8 shows a nuclear imaging system 10. The system 10 is a PET, SPECT, or other imaging system for detecting emissions due to radioactive decay in a patient. The nuclear imaging system 10 may provide qualitative or quantitative imaging.

The system 10 implements the method of FIG. 1, the method of FIG. 2, or other method. Joint estimation in a sequence-based method iteratively solves for values of parameters of a motion model from many (e.g., all) gated projections. A surrogate respiratory signal is used for gating the projections in the joint estimation and the determination of motion in time from the motion model. The estimated motion is used in reconstruction or to motion correct projection data prior to reconstruction.

The nuclear imaging system 10 includes a motion estimation processor 11, a reconstruction processor 12, a memory 14, a display 16, and a detector 18. The processor 11, processor 12, memory 14, and/or display 16 are part of the imaging system with the detector 18 or are separate (e.g., a computer or workstation). Additional, different, or fewer components may be provided. For example, the system 10 is a computer without the detector 18. As another example, user input, patient bed, CT scanner, or other nuclear imaging-related devices are provided. Other parts of the system 10 may include power supplies, communications systems, and user interface systems. In yet another example, the motion estimation processor 11 and the reconstruction processor 12 are formed from the same hardware device.

The detector 18 is a gamma camera connected with a gantry. The gamma camera is a planar photon detector, such as having crystals or scintillators with photomultiplier tubes, SiPM, or another optical detector. Any now known or later developed gamma camera may be used. The gantry rotates the gamma camera about the patient. Alternatively, the detector 18 is a ring of crystals or scintillators with optical detectors. Other structures of detectors may be used. Other components may be provided, such as a collimator.

The nuclear imaging system 10, using the detector 18, detects emissions from the patient 15 for measuring uptake or physiological function. During scanning of a patient, the detector 18 detects emission events. The emissions occur from any location in a finite source (i.e., the patient). The radiotracer in the patient migrates to, connects with, or otherwise concentrates at specific types of tissue or locations associated with specific biochemical reactions. Thus, a greater number of emissions occur from locations of that type of tissue or reaction. With a SPECT detector 18, the emission events are detected at different positions or angles relative to the patient, forming lines of response for the events. With a ring of PET detectors, the emissions are detected along the lines of response without movement of the detector 18. The patient bed may move to define a field of view relative to the patient.

Due to respiratory motion, the location of the lines of response and resulting pixel or sensor of the detector 18 that detects the emission from the same location may be different at different times. The projection data of the detected emissions is subjected to a motion artifact due to respiratory motion.

The motion estimation processor 11 and the reconstruction processor 12 are separate hardware devices, but may be one hardware device configured for different operations. The processors 11, 12 are of a same or different type of device. A general processor, digital signal processor, imaging processor, graphics processing unit, application specific integrated circuit, field programmable gate array, digital circuit, analog circuit, combinations thereof, or other now known or later developed device may be used. Each of the processors 11, 12 is a single device, a plurality of devices, or a network. For more than one device, parallel or sequential division of processing may be used. Different devices making up one of the processors 11, 12 may perform different functions, such as one processor (e.g., application specific integrated circuit or field programmable gate array) for reconstructing the object and another (e.g., graphics processing unit) for rendering an image from the reconstructed image object. In one embodiment, one or both processors 11, 12 are a control processor or other processor of nuclear imaging system 10. In other embodiments, one or both processors 11, 12 are part of a separate workstation or computer. The hardware processors 11, 12 are configured by software, firmware, and/or hardware and operate pursuant to stored instructions to perform various acts described herein.

The motion estimation processor 11 is configured to perform acts 24-28 and 32-34 of FIG. 1, but may perform additional, different, or fewer acts. The motion estimation processor 11 is configured to determine a respiration surrogate signal form the detected emission signals, gate the detected emission signals with the respiration surrogate signal into three or more gated sets, and/or jointly solve for motion in all the gated sets with an iterative solution based on a motion model of the motion. The motion model is a linear or other model. The joint solution uses a maximum likelihood or other iterative solution to solve for the values of parameters of the motion model.

The reconstruction processor 12 is configured to perform acts 30 and 36 of FIG. 1, but may perform additional, different, or fewer acts (e.g., perform acts 32 and 34). The reconstruction processor 12 is configured to reconstruct an image of the detected emission signals from the patient as a function of the estimated motion. The estimated motion is used in reconstruction, such as part of a projection operator for forward projection or part of a system matrix. In other embodiments, the estimated motion is used to correct the detected emission signals prior to reconstruction. The detected emission signals are corrected for motion, and then the motion corrected emission signals are reconstructed.

The reconstruction processor 12 is configured to reconstruct a volume or object from emissions. Any reconstruction may be used to estimate the activity concentration or distribution of the tracer in the patient. The reconstruction processor 12 accesses the corrected detected emission events from the memory 14, from the detector 18, or buffers to reconstruct. The corrected detected emissions are used to reconstruct the distribution of the radioisotope in three dimensions. Forward and backward projection are used iteratively until a merit function indicates completion of the reconstruction (i.e., a best or sufficient match of the image object to the detected emissions).

The reconstruction processor 12 generates one or more images based on the reconstruction. Any given image represents the emissions from the patient. The image shows the spatial distribution, such as with a multi-planar reconstruction or a volume rendering. For quantitative imaging, the image represents accurate measures (e.g., in Bq/ml) of the activity concentration. Alternatively or additionally, the image shows a quantity or quantities (e.g., alphanumeric) representing the activity concentration or specific uptake values for one or more locations or regions.

The display 16 is a CRT, LCD, plasma screen, projector, printer, or other output device for showing an image. The display 16 is configured by a display plane or buffer to display an image of the reconstructed functional volume.

The memory 14 is a buffer, cache, RAM, removable media, hard drive, magnetic, optical, database, or other now known or later developed memory. The memory 14 is a single device or group of two or more devices. The memory 14 is part of the nuclear imaging system 10 or a remote workstation or database, such as a PACS memory.

The detected emission events, counts, locations, gated sets of emission events, values of motion parameters, surrogate respiration signal, and/or other information are stored in the memory 14. The memory 14 may store data at different stages of processing. The data is stored in any format.

The memory 14 is additionally or alternatively a non-transitory computer readable storage medium with processing instructions. The memory 14 stores data representing instructions executable by the programmed processors 11 and/or 12. The instructions for implementing the processes, methods, and/or techniques discussed herein are provided on non-transitory computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for correction of respiratory motion in a nuclear medical imaging system, the method comprising:

detecting, with a nuclear imaging detector, emissions over time from a patient, the detected emissions comprising projection data and are subject to respiration motion of the patient;

gating the projection data into three or more sets;

estimating the respiration motion with an iterative solution of a maximum likelihood objective function based on the gated projection data of the three or more sets, the objective function including a motion model with parameters of the respiration motion;

reconstructing an image object of the patient from the projection data with the respiration motion used to correct the projection data used in reconstruction or used in the reconstructing; and generating an image of the reconstructed image object.

2. The method of claim 1 wherein detecting comprises detecting the emissions with a single photon emission computed tomography or a positron emission tomography system.

3. The method of claim 1 wherein gating comprises gating with a surrogate respiration signal, and wherein correcting comprises correcting as a function of the surrogate respiration signal.

4. The method of claim 3 wherein the surrogate respiration signal is derived from variation in the projection data as a function of time.

5. The method of claim 1 wherein estimating comprises estimating with the parameters of the motion model comprising perpendicular translations of rigid motion between the gated three or more sets.

6. The method of claim 1 wherein estimating based on the gated projection data of the three or more sets comprises estimating with a sequence-based approach.

7. The method of claim 1 wherein estimating comprises estimating with the objective function comprising a minimization of a maximum likelihood of the gated projection data of the three or more sets relative to a reference projection.

8. The method of claim 7 wherein the reference projection comprises a mean of the gated projection data of the three or more sets shifted to a reference location.

9. The method of claim 7 wherein estimating with the iterative solution comprises updating the reference projection in each iteration of the iterative solution.

10. The method of claim 1 wherein estimating with the iterative solution comprises estimating with a Broyden-Fletcher-Goldfarb-Shanno algorithm.

11. The method of claim 1 wherein estimating with the iterative solution comprises estimating with an initial value of one of the parameters of the respiration motion comprising a ratio of a largest difference in center of mass between the sets of the gated projection data to a change in amplitude of a surrogate respiration signal over time.

12. The method of claim 1 wherein the respiration motion is used to correct the projection data with interpolation in a Fourier domain.

13. The method of claim 1 wherein estimating the respiration motion comprises estimating as a function of gates of the three or more sets, and wherein the respiration motion is used to correct the projection data by determining shift as a function of time from the estimated respiration motion for the gates and a surrogate respiration signal as a function of time.

14. The method of claim 1 further comprising masking the projection data as a function of an ellipsoid derived from the projection data.

15. A method for correction of respiratory motion in a single photon emission computed tomography (SPECT) medical imaging system, the method comprising:
respiration gating SPECT emission data of a patient with a surrogate respiration signal into respiration gated sets of SPECT emission data;
jointly estimating two-dimensional motion vectors across the respiration gated sets of SPECT emission data;
determining respiration motion as a function of time from the surrogate respiration signal and the two-dimensional motion vectors; and
generating a SPECT image of the patient from the SPECT emission data and the respiration motion.

16. The method of claim 15 generating comprises reconstructing an image object of the patient (1) with a system matrix using the determined respiration motion or (2) with the SPECT emission data corrected with an inverse of the determined respiration motion as a function of time.

17. The method of claim 15 wherein jointly estimating comprises iteratively solving a maximum likelihood objective function, the iteratively solving including joint solution over three or more of the gated sets, the two-dimensional motion vector comprising a motion model.

18. The method of claim 15 wherein jointly estimating comprises simultaneously fitting the two-dimensional motion vectors across all the respiration gated sets.

19. A nuclear imaging system comprising:
a detector for detecting signals along lines of response from a patient;
a motion processor configured to determine a respiration surrogate signal from the signals, gate the signals with the respiration surrogate signal into three or more gated sets, jointly solve for motion in all the gated sets with iterative solution based on a motion model of the motion;
a reconstruction processor configured to reconstruct an image of the signals from the patient, the image being a function of the motion used in reconstruction or used in correction of the signals; and
a display configured to display the image.

20. The nuclear imaging system of claim 19 wherein the motion model comprises a linear model, wherein the motion processor is configured to jointly solve with a maximum likelihood, and wherein the reconstruction processor is configured to reconstruct the image with the signals with the motion being used in reconstruction.

* * * * *